US008975572B2

(12) United States Patent
Hargis

(10) Patent No.: US 8,975,572 B2
(45) Date of Patent: Mar. 10, 2015

(54) COMPACT, THERMALLY STABLE FIBER-OPTIC ARRAY MOUNTABLE TO FLOW CELL

(75) Inventor: David E. Hargis, San Diego, CA (US)

(73) Assignee: CVI Laser, LLC, Albuquerque, NM (US)

( * ) Notice: Subject to any disclaimer, the term of this patent is extended or adjusted under 35 U.S.C. 154(b) by 1131 days.

(21) Appl. No.: 12/418,494

(22) Filed: Apr. 3, 2009

(65) Prior Publication Data

US 2009/0257054 A1    Oct. 15, 2009

Related U.S. Application Data

(60) Provisional application No. 61/042,640, filed on Apr. 4, 2008.

(51) Int. Cl.
| | |
|---|---|
| G02B 6/42 | (2006.01) |
| G01J 3/10 | (2006.01) |
| G01N 21/64 | (2006.01) |
| G01J 3/02 | (2006.01) |
| G01N 21/05 | (2006.01) |
| G01N 21/31 | (2006.01) |
| G01N 21/03 | (2006.01) |

(52) U.S. Cl.
CPC .............. *G01J 3/10* (2013.01); *G01N 21/6402* (2013.01); *G01N 21/645* (2013.01); *G01J 3/0286* (2013.01); *G01N 21/05* (2013.01); *G01N 21/31* (2013.01); *G01N 2021/6419* (2013.01); *G01N 2021/0346* (2013.01)
USPC .................................. 250/227.25; 250/227.11

(58) Field of Classification Search
USPC ............. 250/227.11, 227.14, 227.17, 227.25, 250/559.4, 458.1, 461.1, 459.1; 356/317, 356/417, 318, 72, 73; 385/8–11
See application file for complete search history.

(56) References Cited

U.S. PATENT DOCUMENTS

| | | | |
|---|---|---|---|
| 4,296,995 A | 10/1981 | Bickel | |
| 4,550,240 A | 10/1985 | Toida et al. | |
| 4,573,465 A | 3/1986 | Sugiyama et al. | |
| 4,632,554 A | 12/1986 | Pearce | |
| 4,722,591 A | 2/1988 | Haffner | |
| 4,817,101 A | 3/1989 | Wyeth et al. | |
| 4,938,593 A | 7/1990 | Morris et al. | |

(Continued)

FOREIGN PATENT DOCUMENTS

| | | |
|---|---|---|
| DE | 41 13 279 | 10/1992 |
| DE | 195 08 754 | 6/1999 |

(Continued)

OTHER PUBLICATIONS

Olympus Confocal Laser Scanning Biological Microscope, FV1000, Fluoview—Always Evolving, available at http://www.olympusamerica.com/files/seg_bio/fv1000_brochure.pdf.

*Primary Examiner* — Que T Le
(74) *Attorney, Agent, or Firm* — Knobbe Martens Olson & Bear LLP

(57) ABSTRACT

Various embodiments of an optical system for directing light for optical measurements such laser-induced fluorescence and spectroscopic analysis are disclosed. In some embodiments, the optical system includes a thermally conductive housing and a thermoelectric controller, a plurality of optical fibers, and one or more optical elements to direct light emitted by the optical fibers to illuminate a flow cell. The housing is configured to attach to a flow cell.

32 Claims, 4 Drawing Sheets

(56) References Cited

U.S. PATENT DOCUMENTS

| | | |
|---|---|---|
| 4,983,042 A | 1/1991 | Korner et al. |
| 5,106,192 A | 4/1992 | Tucker et al. |
| 5,109,447 A | 4/1992 | Can |
| 5,147,349 A | 9/1992 | Johnson et al. |
| 5,152,759 A | 10/1992 | Parel et al. |
| 5,258,989 A | 11/1993 | Raven |
| 5,260,578 A | 11/1993 | Bliton et al. |
| 5,289,557 A | 2/1994 | Sheinis et al. |
| 5,295,143 A | 3/1994 | Rao et al. |
| 5,304,167 A | 4/1994 | Freiberg |
| 5,325,393 A | 6/1994 | Nighan, Jr. et al. |
| 5,343,038 A | 8/1994 | Nishiwaki et al. |
| 5,394,492 A | 2/1995 | Hwang |
| 5,446,532 A | 8/1995 | Yamazaki |
| 5,491,344 A * | 2/1996 | Kenny et al. ............... 250/461.1 |
| 5,544,271 A | 8/1996 | Lim |
| 5,617,500 A | 4/1997 | Shionoya et al. |
| 5,633,695 A | 5/1997 | Feke et al. |
| 5,659,642 A | 8/1997 | King et al. |
| 5,668,903 A | 9/1997 | Neuberger et al. |
| 5,674,698 A | 10/1997 | Zarling et al. |
| 5,698,397 A | 12/1997 | Zarling et al. |
| 5,736,410 A | 4/1998 | Zarling et al. |
| 5,771,325 A | 6/1998 | Neuberger |
| 5,814,820 A | 9/1998 | Dong et al. |
| 5,823,942 A | 10/1998 | Toida |
| 5,824,269 A | 10/1998 | Kosaka et al. |
| 5,866,911 A | 2/1999 | Baer |
| 5,952,668 A | 9/1999 | Baer |
| 6,048,444 A | 4/2000 | Takahashi et al. |
| 6,081,544 A | 6/2000 | Zamel et al. |
| 6,101,201 A | 8/2000 | Hargis et al. |
| 6,110,165 A | 8/2000 | Ota |
| 6,133,995 A | 10/2000 | Kubota |
| 6,175,440 B1 | 1/2001 | Conemac |
| 6,214,033 B1 | 4/2001 | Ii et al. |
| 6,215,807 B1 | 4/2001 | Reilly |
| 6,221,671 B1 | 4/2001 | Groner et al. |
| 6,222,961 B1 | 4/2001 | Engelhardt et al. |
| 6,462,345 B1 | 10/2002 | Simon et al. |
| 6,480,513 B1 | 11/2002 | Kapany et al. |
| 6,490,309 B1 | 12/2002 | Okazaki et al. |
| 6,510,001 B1 | 1/2003 | Engelhardt et al. |
| 6,557,369 B1 * | 5/2003 | Phelps et al. ............... 62/457.5 |
| 6,592,822 B1 | 7/2003 | Chandler |
| 6,603,780 B2 | 8/2003 | Miyai |
| 6,614,031 B2 | 9/2003 | Engelhardt et al. |
| 6,654,165 B2 | 11/2003 | Engelhardt et al. |
| 6,677,566 B2 | 1/2004 | Knebel et al. |
| 6,737,635 B2 | 5/2004 | Engelhardt et al. |
| 6,750,457 B2 | 6/2004 | Heffelfinger et al. |
| 6,836,489 B2 | 12/2004 | Nishimura et al. |
| 6,867,899 B2 | 3/2005 | Knebel |
| 6,867,919 B2 | 3/2005 | Seyfried |
| 6,920,159 B2 | 7/2005 | Sidorin et al. |
| 6,958,470 B2 | 10/2005 | Hoffmann |
| 6,980,293 B1 | 12/2005 | Harada |
| 7,005,654 B2 | 2/2006 | Seyfried |
| 7,098,447 B2 | 8/2006 | Moellmann |
| 7,133,130 B2 | 11/2006 | Storz et al. |
| 7,151,633 B2 | 12/2006 | Storz et al. |
| 7,280,567 B2 | 10/2007 | Luo et al. |
| 7,280,570 B2 | 10/2007 | Seyfried et al. |
| 7,330,493 B2 | 2/2008 | Luo et al. |
| 7,394,063 B2 | 7/2008 | Schreiber |
| 7,426,027 B2 * | 9/2008 | Noguchi et al. ............... 356/317 |
| 7,428,104 B2 | 9/2008 | Engelhardt |
| 7,430,231 B2 | 9/2008 | Luo et al. |
| 7,433,119 B2 | 10/2008 | Gugel |
| 7,457,300 B2 | 11/2008 | Luo et al. |
| 7,468,998 B2 | 12/2008 | Luo et al. |
| 7,474,462 B2 | 1/2009 | Ulrich et al. |
| 7,505,495 B2 | 3/2009 | Fratti et al. |
| 7,522,651 B2 | 4/2009 | Luo et al. |
| 7,535,937 B2 | 5/2009 | Luo et al. |
| 7,535,938 B2 | 5/2009 | Luo et al. |
| 7,542,489 B2 | 6/2009 | Luo et al. |
| 7,548,567 B2 | 6/2009 | Kupershmidt et al. |
| 7,564,624 B2 | 7/2009 | Leimbach et al. |
| 7,599,115 B2 | 10/2009 | Gugel |
| 7,599,413 B2 | 10/2009 | Luo et al. |
| 7,606,273 B2 | 10/2009 | Zhu et al. |
| 7,633,979 B2 | 12/2009 | Luo et al. |
| 7,660,035 B2 | 2/2010 | Bohm et al. |
| 7,724,363 B2 | 5/2010 | Wachsmuth et al. |
| 7,733,932 B2 | 6/2010 | Faybishenko |
| 7,742,226 B2 | 6/2010 | Bewersdorf et al. |
| 7,813,390 B2 | 10/2010 | Luo et al. |
| 7,835,601 B2 | 11/2010 | Seyfried et al. |
| 7,899,105 B1 | 3/2011 | Hargis et al. |
| 7,903,706 B2 | 3/2011 | O'Shaughnessy et al. |
| 7,949,025 B2 | 5/2011 | Olea |
| 7,999,935 B2 | 8/2011 | Dyba |
| 8,238,389 B2 | 8/2012 | Hargis et al. |
| 2001/0017868 A1 | 8/2001 | Kraenert et al. |
| 2001/0021210 A1 | 9/2001 | Nakaya et al. |
| 2002/0061032 A1 | 5/2002 | Miura et al. |
| 2002/0097772 A1 | 7/2002 | Dautremont-Smith et al. |
| 2003/0058530 A1 | 3/2003 | Kawano |
| 2003/0214987 A1 | 11/2003 | Yamanaka et al. |
| 2004/0027631 A1 | 2/2004 | Nagano et al. |
| 2004/0210289 A1 | 10/2004 | Wang et al. |
| 2005/0180474 A1 | 8/2005 | Buchold et al. |
| 2005/0201441 A1 | 9/2005 | Seyfried et al. |
| 2005/0220458 A1 | 10/2005 | Kupershmidt et al. |
| 2005/0281298 A1 | 12/2005 | Kupershmidt et al. |
| 2006/0097188 A1 | 5/2006 | Seyfried |
| 2006/0239317 A1 | 10/2006 | Yoshida et al. |
| 2006/0245049 A1 | 11/2006 | Knebel |
| 2006/0273260 A1 | 12/2006 | Casstevens et al. |
| 2007/0024978 A1 | 2/2007 | Jackson et al. |
| 2008/0025677 A1 | 1/2008 | Sasaki |
| 2008/0089369 A1 | 4/2008 | Luo et al. |
| 2009/0097507 A1 | 4/2009 | Zhu et al. |
| 2009/0257054 A1 | 10/2009 | Hargis |
| 2009/0274176 A1 | 11/2009 | O'Shaughnessy et al. |
| 2009/0323203 A1 | 12/2009 | Adams et al. |
| 2010/0006772 A1 | 1/2010 | Gugel |
| 2010/0073757 A1 | 3/2010 | Birk et al. |
| 2010/0111768 A1 | 5/2010 | Banerjee et al. |
| 2010/0177375 A1 | 7/2010 | Seyfried |
| 2010/0232011 A1 | 9/2010 | Seyfried |
| 2011/0222054 A1 | 9/2011 | Krishnamachari |
| 2011/0273768 A1 | 11/2011 | Krishnamachari et al. |

FOREIGN PATENT DOCUMENTS

| | | |
|---|---|---|
| JP | 07 318810 | 12/1995 |
| WO | WO 2010/065779 | 6/2010 |

\* cited by examiner

COMPACT, THERMALLY STABLE FIBER-OPTIC ARRAY MOUNTABLE TO FLOW CELL

CROSS-REFERENCE TO RELATED APPLICATIONS

This application claims the benefit of U.S. Provisional Application No. 61/042,640, filed Apr. 4, 2008, which is incorporated by reference in its entirety.

BACKGROUND OF THE INVENTION

1. Field of the Invention

This disclosure relates generally to optical systems for directing light to a sample contained in a flow cell, and more particularly to a compact, thermally stable, optical fiber array attachable to a flow cell for directing laser light to the flow cell for optical measurements such as laser-induced fluorescence.

2. Description of the Related Art

Optical analysis of flow cells, such as laser-induced fluorescence, involves illuminating biological samples with laser light in order to test samples which may, for example, be tagged with fluorescent dyes. Fluorescent dyes absorb light at certain wavelengths and in turn emit their fluorescence energy at a different wavelength. This emission can be detected to ascertain properties of the fluid in the flow cell. Existing systems for fluorescent analysis of flow cells, however, suffer from various drawbacks, such as measurement error.

SUMMARY OF THE INVENTION

Embodiments described herein have several features, no single one of which is solely responsible for their desirable attributes. Without limiting the scope of the invention as expressed by the claims, some of the advantageous features will now be discussed briefly.

Various embodiments described herein provide the ability to perform optical measurements on flow cells while addressing some of the drawbacks encountered with conventional approaches, such as temperature instability and the resultant pointing errors and signal power fluctuations. A wide range of embodiments, however, are disclosed.

Various embodiments disclosed herein, for example, comprise a laser system for directing light for optical measurements, such as laser-induced fluorescence. The laser system can include a thermally conductive housing defining an interior chamber, and a thermoelectric controller thermally coupled to the housing. The laser system can include a plurality of optical input ports, and the optical input ports can be configured to engage a plurality of input optical fibers and receive light from the input optical fibers. The laser system can include a plurality of optical fibers contained within the interior chamber, and the optical fibers can be configured to receive the light from the optical input ports and output the light into the internal chamber. The laser system can include one or more optical elements configured to receive the light output by the optical fibers and output a plurality of beams of light. The laser system can include a flow cell connector configured to attach a flow cell to the housing, and the flow cell connector can be configured to position the flow cell to intersect the beams of light.

The thermoelectric controller can be configured to maintain the interior chamber at a substantially constant temperature.

The plurality of beams of light produced by the one or more optical elements can comprise a plurality of substantially elliptical beams of light. The one or more optical elements can comprise a plurality of anamorphic microlenses. The laser system can include one or more output windows, and the one or more output windows can be configured to transmit the beams of light out of the internal chamber.

The flow cell connector can be configured to attach the flow cell to the outside of the housing. The housing can be hermetically sealed.

The plurality of input ports can be configured to removably engage the plurality of input optical fibers. The plurality of input ports can comprise a plurality of FC connectors. The plurality of input ports can comprise a plurality of angle-polished connections.

The plurality of optical fibers can comprise a plurality of input ends and a plurality of output ends, with the input ends being distributed across a first distance and the output ends being distributed across a second distance, wherein the first distance is greater than the second distance. Each output end can comprise a center, and the centers can be spaced about 110 to 140 micrometers apart. The one or more optical elements can be configured to produce the beams of light spaced about 110 to 140 micrometers apart. The centers can be spaced about 125 micrometers apart, and the one or more optical elements can be configured to produce the beams of light spaced about 125 micrometers apart. The plurality of optical fibers can be polarization-maintaining optical fibers.

The laser system of can include a plurality of input optical fibers coupled to the optical input ports, and a plurality of laser light sources coupled to the input optical fibers.

The laser system can include a flow cell attached to the housing via the flow cell connector, and the flow cell can be configured to direct a sample fluid into the beams of light. The flow cell connector can comprise thermally conducting material, and the flow cell connector can be thermally coupled to the thermoelectric controller, and the thermoelectric controller can be configured to maintain the flow cell at a substantially constant temperature.

The one or more optical elements can be formed in the housing, the one or more optical elements configured to transmit the light out of the internal chamber, and the flow cell connector can be configured to attach the flow cell to the outside of the housing.

The flow cell connector can be configured to attach the flow cell to the housing with the flow cell passing through the interior chamber, and the flow cell connector can comprise at least one seal configured to form a seal around the flow cell.

Various embodiments disclosed herein comprise a laser system for directing light for optical measurements. The laser system can include a thermally conductive housing defining an interior chamber, and a thermoelectric controller thermally coupled to the housing. The laser system can include a plurality of optical input ports, and the optical input ports can be configured to engage a plurality of input optical fibers and receive light from the input optical fibers. The laser system can include a plurality of waveguides contained within the interior chamber, and the waveguides can be configured to receive the light from the optical input ports and output the light into the internal chamber. The laser system can include one or more optical elements configured to receive the light output by the waveguides and output a plurality of beams of light. The laser system can include a flow cell connector configured to attach a flow cell to the housing, and the flow cell connector can be configured to position the flow cell to intersect the beams of light.

Various embodiments disclosed herein comprise a laser system for directing light for optical measurements. The laser system can include a plurality of optical fibers for receiving light from a plurality of lasers, and the optical fibers can have a plurality of output ends, and each output end can include a center. The laser system can include an optical fiber mount configured to orient the plurality of optical fibers with the centers of said output ends spaced about 110 to 140 microns apart. The laser system can include a flow cell connector configured to position a flow cell forward the output ends. The optical fiber mount can be configured to orient the plurality of optical fibers with the centers of the output ends spaced about 125 microns apart.

Various embodiments disclosed herein comprise a laser system for directing light for optical measurements. The laser system can include a flow cell configured to provide a sample fluid for measurement, and a plurality of optical fibers for receiving light from a plurality of lasers. The optical fibers can have a plurality of output ends. The laser system can include an optical fiber mount configured to orient the plurality of optical fibers with the output ends positioned to emit light toward said flow cell.

BRIEF DESCRIPTION OF THE DRAWINGS

The following drawings and the associated descriptions are provided to illustrate embodiments of the present disclosure and do not limit the scope of the claims.

DETAILED DESCRIPTION OF THE PREFERRED EMBODIMENT

Embodiments of the inventions will now be described with reference to the accompanying figures. Although certain preferred embodiments and examples are disclosed herein, inventive subject matter extends beyond the specifically disclosed embodiments to other alternative embodiments and/or uses of the inventions, and to modifications and equivalents thereof. Thus, the scope of the inventions herein disclosed is not limited by any of the particular embodiments described below. For example, in any method or process disclosed herein, the acts or operations of the method or process may be performed in any suitable sequence and are not necessarily limited to any particular disclosed sequence.

For purposes of contrasting various embodiments with the prior art, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 1:
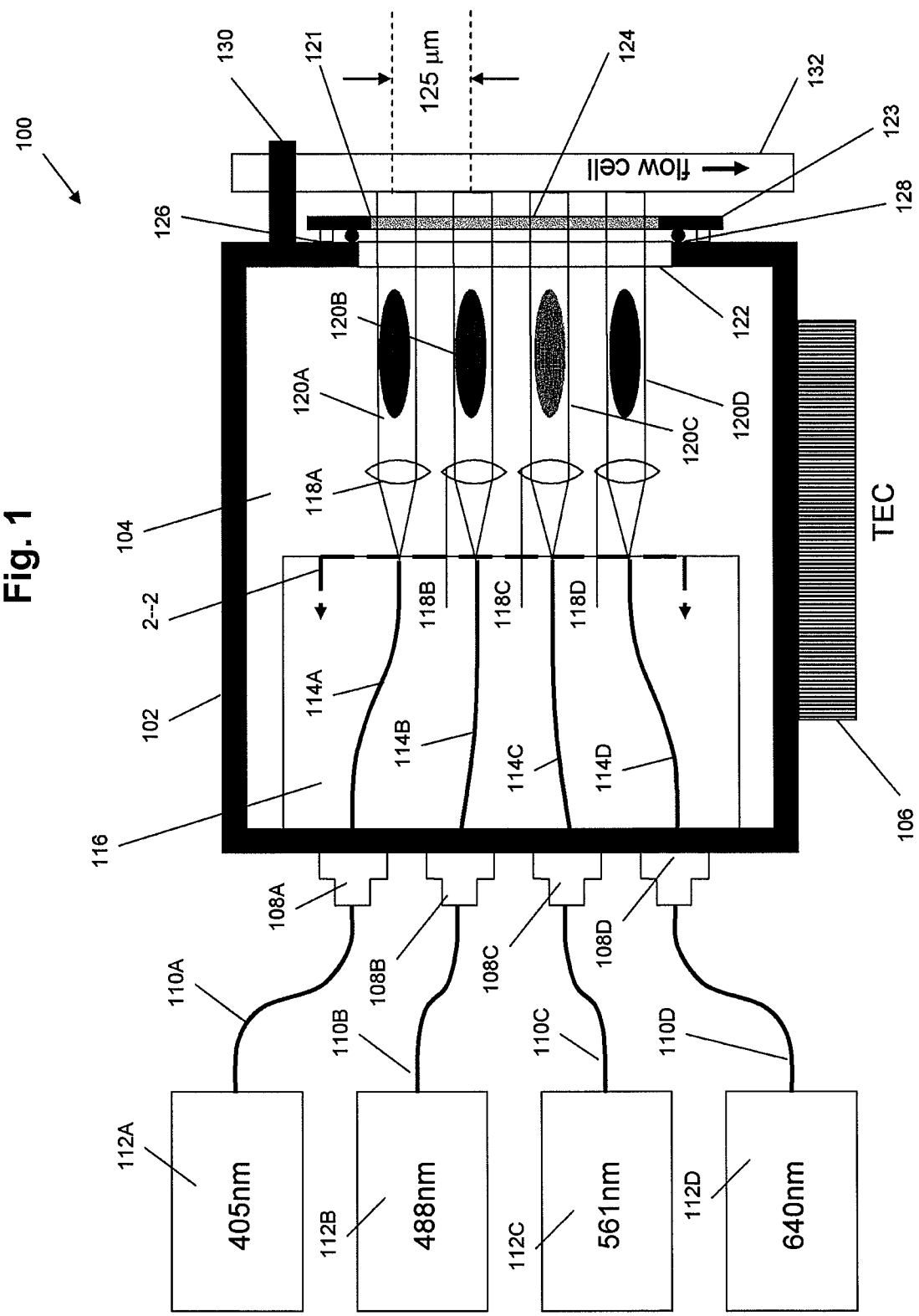
FIG. 1 schematically shows an optical system that can be used to direct light to samples for performing optical measurements such as laser-induced fluorescence and spectroscopic analysis.

FIG. 1 schematically shows an optical system 100 that can be used to direct light to a sample for performing optical measurements such as laser-induce fluorescence and spectroscopic analysis. The optical system 100 can include a housing 102 enclosing an interior chamber 104. The housing 102 can be made of a thermally conductive material. The thermally conductive material can have a thermal conductivity between about 50 W/(m-K) and about 2000 W/(m-K). For example, the thermally conductive material may be copper which has a thermal conductivity of about 380 W/(m-K). A variety of thermally conductive metals can be used (e.g., copper or aluminum), as well as thermally conductive non-metals (e.g., ceramics or epoxy). The thermally conductive material can be used to form the entire housing, or merely a portion thereof. For example, substantially thermally conductive material can be used to form the top, the bottom, or any number of the sides of the housing 102, or any combination thereof. In some embodiments, a majority of the housing 102 is made of the substantially thermally conductive material. In some embodiments, only a relatively small portion of the housing 102 is made of the substantially thermally conductive material. In some embodiments, a substantial portion of the housing 102 is made of the substantially thermally conductive material. In some embodiments, multiple substantially thermally conductive materials can be used, with some areas of the housing 102 being more thermally conductive than others.

In some of the embodiments discussed above, the housing is hermetically sealed from the ambient air. Thus, the interior chamber 104 is isolated from air currents which can cause temperature variation, and the internal optical elements are protected from external contaminants. In some embodiments a getter (not shown) is located inside interior chamber 104 which can reduce contaminant particles or chemical species. Additional, a desiccant (not shown) can be positioned inside the interior chamber 104 to reduce moisture.

A thermoelectric controller 106 can be thermally coupled to the housing 102. The thermoelectric controller 106 can include one or more temperature sensors (not shown) (e.g., thermistors) to measure the temperature of the housing 102 and/or the temperature of the interior chamber 104, and a heat transfer system (not shown) for removing heat from or adding heat to the housing 102 in order to maintain a substantially constant temperature in the housing or in the interior chamber. In some embodiments, the thermoelectric controller 106 can include a cooler for removing heat (e.g., heat resulting from operation of the optical system). In some embodiments, the thermoelectric controller 106 can include a heater for heating the housing 102 and internal chamber 104. In some embodiments, the heater can be used to maintain the internal chamber 104 at a temperature above the anticipated highest ambient temperature. In some embodiments, the thermoelectric controller 106 can include a thermoelectric cooler (TEC). The heat transfer system can be coupled directly to the housing 102 and to the cooler and/or heater (e.g. TEC). In some embodiments, the temperature can be held within held within ±1° C., ±2° C., ±3° C., ±5° C., etc. of the target temperature. In some embodiments, the temperature of the interior chamber 104 is between 15° C. and 45° C.

In some embodiments, the housing is compact. For example, the housing may be a size of less than 10 cubic inches. The relatively small size of the volume allows for rapid adjustment of temperature in response to variations in the ambient temperature and thus more precise control of the temperature in the internal chamber 104.

The optical system 100 can include a number of optical input ports 108A-108D. Although the embodiment shown in FIG. 1 includes four optical input ports, a different number of optical input ports can be used. In some embodiments, the optical input ports 108A-108D can be secured and hermetically sealed into respective apertures formed in the housing 102, and can engage optical fibers 110A-110D. A variety of fiber connectors can be used, such as screw-type optical fiber connectors (e.g., an FC connector), snap-type fiber connectors, or other fiber connectors known in the art or yet to be devised. In some embodiments, the optical input ports 108A-108D include an angle-polished fiber connector (e.g., an FC/APC connector). In some embodiments, at least a portion of the optical input ports 108A-108D, such as the threading of a screw-type connector, can be integrally formed as part of the housing 102. The optical fibers 110A-110D include fiber connectors (not shown) configured to securely and precisely mate with the optical input ports 108A-108D so that light can be efficiently transferred from the optical fibers 110A-110D to a plurality of optical fibers 114A-114D within the internal chamber 104. In some embodiments, the optical fibers 110A-110D are single mode optical fibers. Highly polarized light can be injected into the optical fibers 110A-110D (e.g., from a diode laser), and in some applications it can be advantageous to preserve the polarization of the light. Accordingly, polarization-maintaining optical fibers can be used. In some embodiments different types of optical fibers can be connected to different optical input ports 108A-108D. Likewise, in some embodiments, the different optical input ports 108A-108D can comprise different types of optical connectors.

The optical fibers 110A-110D can be coupled to laser light sources 112A-112D. Although the embodiment shown in FIG. 1 includes four lasers, a different number of lasers can be used. The lasers 112A-112D can include a variety of different laser types and can provide light of variety of different wavelengths. The optical system 100 shown in FIG. 1 includes a 405 nm laser, a 488 nm laser, a 561 nm laser, and a 640 nm laser, but other common wavelengths of laser light can be used (e.g., light having a wavelength of 440 nm, 635 nm, or 375 nm). The lasers 112A-112D can be diode lasers, diode-pumped solid state lasers, frequency doubled lasers, or other laser types that produce light useful for example in laser-induced fluorescence and spectroscopic analysis. Although FIG. 1 shows the lasers 112A-112D connected to the optical input ports 108A-108D via the optical fibers 110A-110D, in some embodiments the optical fibers 110A-110D and the lasers 112A-112D can be disconnected from the optical input ports 108A-108D by the user so that other lasers can be interchangeably connected to the optical system 100. Thus, the optical system 100 is a versatile tool which a user can easily modify to utilize a wide variety of lasers without difficult and time consuming adjustments.

The optical system 100 can include a plurality of optical fibers 114A-114D contained within the internal chamber 104. The optical fibers 114A-114D can be optically coupled to the optical input ports 108A-108D so that they receive light from the optical input ports 108A-108D and direct the light into the internal chamber 104. In some embodiments, the cores of the optical fibers 114A-114D can be exposed by optical input ports 108A-108D so that the cores of the optical fibers 110A-110D can contact the cores of the optical fibers 114A-114D directly or come in substantial proximity to the cores of optical fibers 114A-114D. As with the optical fibers 110A-110D discussed above, the optical fibers 114A-114D can be single mode optical fibers and can be polarization-maintaining optical fibers.

In some embodiments, the optical system can include a fiber support structure 116 that is configured to change the pitch of the optical fibers 114A-114D, bringing the output ends closer together than the input ends. For example, the optical input ports 108A-108D can be spaced about 10 to 20 millimeters or more apart from each other, so that the user can conveniently connect and disconnect optical fibers. The input ends of the optical fibers 114A-114D, which are coupled to the optical input ports 108A-108D, can be similarly distributed for example about 10 to 20 millimeters or more apart. The fiber support structure 116 can have grooves (e.g., V-grooves) defining generally converging pathways, and the optical fibers 114A-114D can be secured in the grooves by a top-plate positioned over the grooves or by an adhesive. In some embodiments, the V-grooves can be configured to precisely hold the fibers. In some embodiments, silicon V-grooves manufactured using silicon processing techniques (e.g., etching, photoresists, etc.) can be used to secure the optical fibers 114A-114D. Grooves, holes, or slots for supporting the optical fibers 114A-114D may be formed in a support material (e.g., aluminum) by a machining process, such as electrical discharge machining (EDM). The fiber support structure 116 can be configured to bring the optical fibers 114A-114D closer together so that when the light is output from the optical fibers 114A-114D the light is emitted from nearby locations (e.g., about 110 to 140 microns apart, and more specifically, about 125 microns apart, although other distances are possible).

Figure 2:
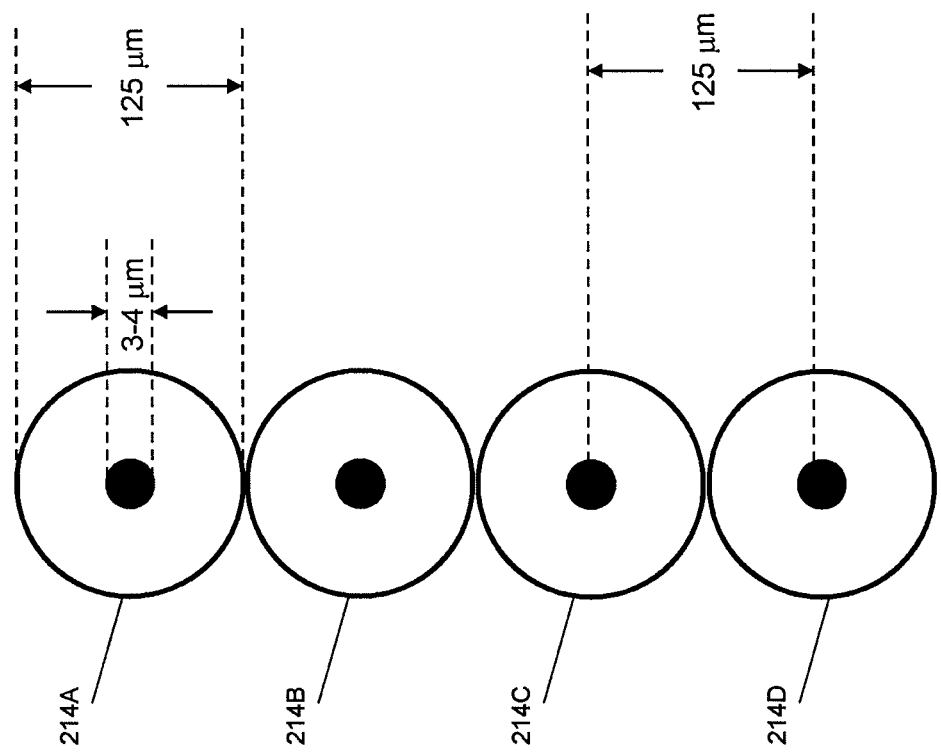
FIG. 2 is a cross-sectional view of an embodiment of an optical fiber array.

FIG. 2 is a cross-sectional view (shown from the position indicated by line 2-2 in FIG. 1) of an embodiment of optical fibers 214A-214D. As shown in FIG. 2, the optical fibers 214A-214D can be single mode optical fibers that have output ends measuring about 125 microns in total diameter, with the core measuring about 3-4 microns in diameter. Other sizes can be used. In the embodiment shown in FIG. 2, the output ends of the optical fibers 214A-214D are brought close together so that the cladding of one optical fiber is adjacent to the cladding of the next optical fiber, and light is emitted by the cores of optical fibers 214A-214D at locations which have centers positioned about 125 microns apart. Other arrangements are possible. It should be noted that the drawings herein are not drawn to scale (unless otherwise indicated), and in some embodiments the tapering of the optical fibers provided by the fiber support structure 116 can be much more pronounced than is indicated in FIG. 1.

In some embodiments, the fiber support structure 116 does not bring the optical fibers 114A-114D significantly closer together, but merely orients the optical fibers 114A-114D so that light is emitted in a direction that causes the light to contact the optical elements 118A-118D at a suitable angle. Other variations are possible.

Although the embodiment illustrated by FIG. 1 includes optical fibers 114A-114D, other types of waveguides can be used (e.g., planar waveguides). In some embodiments, the waveguides can be rigid waveguides. The waveguides can include curved and/or linear paths. The waveguides can include a taper to otherwise have an output end with outputs closer together than inputs at an input end, similar to the embodiment shown in FIG. 1. In some embodiments, an integrated waveguide chip is used.

Although the embodiment illustrated in FIG. 1 shows the optical fibers 110A-110D and the optical fibers 114A-114D as being different sets of optical fibers, in some embodiments, the optical system can include a single set of optical fibers that extend through the housing and couple to the laser light sources. In these embodiments, the optical input ports 108A-108D can be apertures in the housing 102 through which the optical fibers can pass. In some embodiments, the apertures can include seals formed around the optical fibers to hermetically seal the interior chamber. Epoxy may be used to provide such a hermetic seal, although other approaches can be used.

The optical fibers can include optical connectors (e.g., FC/APC connectors) configured to removably couple with the laser light sources 112A-112D.

The optical fibers 114A-114D (or waveguides) emit light toward a plurality of optical elements 118A-118D, which convert the light into beams of light 120A-120D having a suitable shape and/or size. The optical elements 118A-118D can be lenses, and can be separate individual lenses, or they can be conjoined forming a lens array. In some embodiments, optical elements 118A-118D can be compact microlenses. In some embodiments, a single lens can be used to produce each of the light beams 120A-120D. In some applications, it can be advantageous to produce elongated beams of light, such as beams of light having a generally elliptical cross-sectional shape (shown schematically in FIG. 1). For example, the beams of light 120A-120D can have a generally Gaussian profile, so that when illuminating a flow cell, the intensity of the light illuminating the center of the flow cell is significantly greater than the intensity of the light illuminating the peripheral edges of the flow cell. Accordingly, the beams of light 120A-120D can be elongated (e.g., elliptical) beams, so that the relatively high intensity center regions of the light beams extend across the entire width of the flow cell, while the relatively low intensity outer regions of the light beams do not strike the flow cell. By using an elongated (e.g., elliptical) beam of light, a more uniform lateral distribution of light across the narrow width of the flow cell can be achieved while illuminating a relatively small longitudinal area along the length of the flow cell and maintaining high light intensity. In some embodiments, the elliptical light beams can have a substantially elliptical cross sectional shape that measure about 5 to 15 microns in one direction and 55 to 100 microns in the other direction, or more specifically about 10 microns in one direction and about 70 microns in the other direction. Light beams of other shapes and sizes can be used. To produce elongated (e.g., elliptical) beams of light 120A-120D, optical elements 118A-118D can be anamorphic lenses (e.g., cylindrical lenses) or Powell lenses (Gaussian to flat-top transformers). In one embodiment, optical elements 118A-118D can be an anamorphic microlens array. In some embodiments, the optical elements 118A-118D can be achromatic lenses. In some embodiments, optical elements 118A-118D can be refractive and/or diffractive optical elements used to produce the elongated beams of light 120A-120D. In some embodiments, the optical elements 118A-119D can be located adjacent to the output ends of the optical fibers 114A-114D.

The optical system 100 can include an output window 121 that allows the beams of light 120A-120D to exit the internal chamber 104. In some embodiments, the housing 102 includes an aperture 122 in a wall thereof and the output window 121 comprises a transparent window pane 124, positioned over the aperture 122. The window pane 124 can be made from glass or acrylic or a variety of other transparent materials (e.g., plastic). The aperture 122 and window pane 124 can assume a variety of shapes, but in some embodiments they are circular or elliptical. The window 121 can be attached to the housing 102 by a plurality of fasteners such as bolts 126. In FIG. 1, only two bolts 126 are shown in the cross-sectional view, but in some embodiments, additional bolts can be positioned along the edges of the window 121. In some embodiments, the window 121 can include a flange 123 for mounting the window. The flange 123 may have a plurality of through holes through which fasteners (e.g., bolts 126) can pass to secure the window 121 to the housing 102. A seal 128 (e.g., an O-ring) can be positioned between the housing 102 and the window 121 (e.g., the flange 123). The bolts 126 can be tightened, causing the O-ring 128 to be compressed between the housing 102 and the window 121. In some embodiments, the O-ring 128 produces a hermetic seal. Other approaches can be used to fasten the window 121 to the housing 102. For example, the window 121 can be disposed in recess on the outer or inner surface of the housing 102, or can be embedded into the housing 102, or can be mounted onto the inside of the housing 102. The window 121 can be secured to the housing 102 by an adhesive, epoxy, or cement.

Although the embodiment shown in FIG. 1 shows a single output window, multiple output windows can be used. For example, each beam of light 120A-120D can exit the interior chamber 304 via a respective output window. In some embodiments, it is desirable that as much as possible of at least the inner surface area of the housing 102 comprise the thermally conductive material, to better achieve temperature uniformity. Accordingly, the output windows can be separated by thermally conductive material and can cover only as much area as necessary to allow light beams 120A-120D to leave the interior chamber 104. However, in some embodiments a single output window is easier and less expensive to construct.

In some embodiments, the optical elements (e.g., lenses or lens) that produce the light beams 120A-120D can be formed as part of the output window (or windows). For example, the window pane 124 can include at least one curved surface to produce optical power, which can be configured to produce the plurality of light beams 120A-120D having a desired shape and/or size. The window pane 124 can comprise a lens array such as a microlens array, and can be anamorphic as discussed above.

The optical system 100 can include a flow cell connector 130 that is attached to the housing, and the flow cell connector 130 is configured to secure a flow cell 132 so that it intersects the beams of light 120A-120D. In some embodiments, the flow cell connector 130 can permanently attach the flow cell 132 to the housing 102. However, in some embodiments, the flow cell connector 130 can allow the flow cell 132 to be removably attached to the housing 102. In some embodiments, the flow cell connector 130 can be compatible with multiple types and/or sizes of flow cells. For example, the flow cell connector can include a clip, a friction or pressure fit coupling, a threaded portion configured to receive a corresponding threaded portion of the flow cell 132, or a variety of other connectors known in the art or yet to be devised. The flow cell 132 can be a capillary flow cell, and at least part of the flow cell can comprise a transparent material (e.g., glass) that allows the light beams 120A-120D to enter the flow cell 132 and interact with a sample fluid contained within the flow cell 132. In one embodiment, the flow cell 132 can be a thin hollow tube, forming a flow path that has a diameter of about 10 microns. Other flow cell types and/or sizes can be used, and the flow cell 132 can be oriented differently than as shown in FIG. 1. In some embodiments, the beams of light 120A-120D strike the flow cell over areas centered about 110 to 140 microns apart from each other, and in some embodiments, 125 microns apart from each other. For some forms of optical measurements, it is desirable for the laser light to strike the flow cell at specific locations (e.g., areas spaced about 125 microns apart). In some embodiments, the optical system 100 mounts the optical fibers to automatically direct the light from the laser light sources 112A-112D to the desired locations of the flow cell 132 without requiring the user to manipulate any mirrors or wavelength selective elements such as dichroic mirrors or optical elements.

The optical system 100 can be compatible with various types of optical (e.g., spectroscopic) analysis. For example, for laser-induced fluorescence spectroscopy, a fluorescent dye designed to bond with an analyte can be introduced into the fluid sample. When the fluid sample passes through the beams of light 120A-120D, the fluorescent dye absorbs photons and emits photons that have a longer wavelength (less energy). By using photodetectors such as a photomultiplier tube (PMT) (not shown) to measure the amount of light that is emitted, the presence or concentration of the analyte in the sample fluid can be measured. For absorption spectroscopy, photodetectors (not shown) can be positioned on the side of the flow cell 132 opposite the housing 102 to determining the amount of light that is absorbed by the fluid sample. The optical system 100 can also be compatible with other types of optical measurements or spectroscopic analysis.

Figure 3:
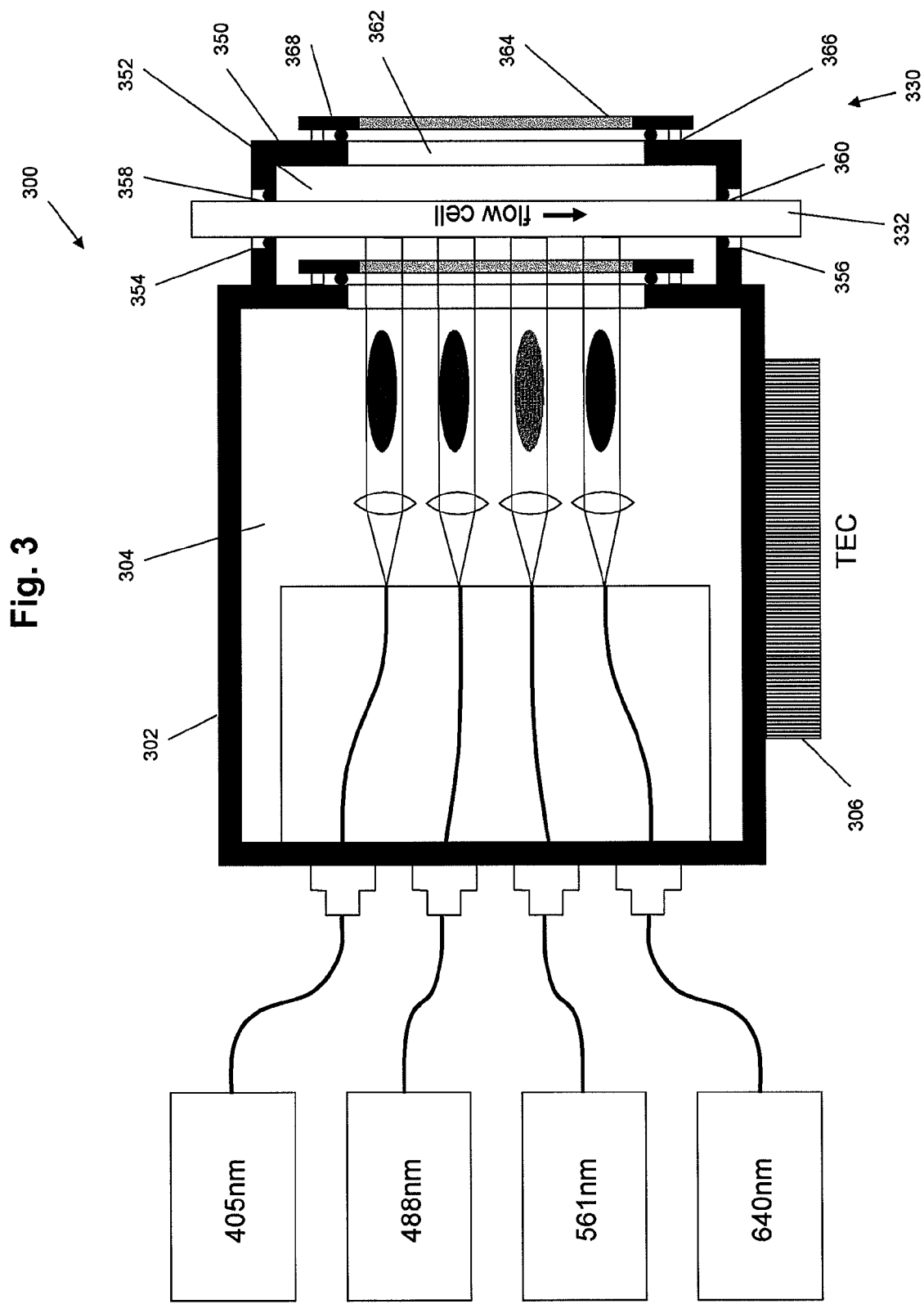
FIG. 3 schematically shows another optical system that can be used to direct light to samples for performing optical measurements such as laser-induced fluorescence and spectroscopic analysis.

FIG. 3 schematically shows an embodiment of an optical system 300 that can be used to direct light for optical measurements (e.g., laser-induced fluorescence and spectroscopic analysis). The optical system 300 is similar to optical system 100 in some aspects, and similar elements are labeled with the same reference numerals used in FIG. 1 except that the numbers are increased by 200. The optical system 300 can include a flow cell connector 330 that comprises a thermally conductive auxiliary sample housing 350 which encloses an interior chamber 352. The flow cell connector 330 can be configured to secure a flow cell 332 so that it passes through the interior chamber 352. For example, the sample housing 350 can include two apertures 354, 356 and two flexible seals 358, 360, so that the flow cell 332 can be slidably inserted through the apertures 354, 356 and held in place by friction against the flexible seals 358, 360. Alternatively, the sample housing 350 can include a door allowing the sample housing 350 to be opened and the flow cell 332 to be placed inside. In various embodiments where the interior chamber 352 of sample housing 350 is hermetically sealed with respect to interior chamber 304 of the main housing 302, the interior chamber 352 of the sample housing 350 can be exposed to ambient air without exposing the components contained within interior chamber 304 of the main housing 302. Accordingly, the interior chamber 352 of the sample housing 350 can be exposed to ambient air when flow cell 332 is removed and the seals 358, 360 may be excluded in some embodiments.

In some embodiments, the sample housing 350 can be integrally formed as part of the main housing 302 or can be thermally coupled to the main housing 302 so that the thermoelectric controller 306 regulates the temperature within the interior chamber 352 of the sample housing 350 as well as the interior chamber 304 of the main housing 302. In some applications it may be desirable to maintain the internal chamber 352 of the sample housing 352 enclosing the flow cell at a different temperature than the internal chamber 304 of the main housing 302, such as when a fluid sample is used that should be maintained at a different temperature than the interior chamber 304 of the main housing 302. Accordingly, in some embodiments, a second thermoelectric controller (not shown) can be thermally coupled to the sample housing 350 and an insulating layer (not shown) can be positioned at the transition between the main housing 302 and the sample housing 350 so that the internal chamber 352 of the sample housing 350 can be maintained at a different temperature than the interior chamber 304 of the main housing 302.

The optical system 300 can include a second output window for transmitting light out of the internal chamber 352 of the sample housing 350. The second output window can be similar to the output window described above, and cover an aperture 362 covered with a transparent window pane 364. The transparent window pane 364 can be attached to the housing 350 by bolts 366 and sealed by a seal 368. In some embodiments, the interior chamber 352 of the sample housing 350 is not hermetically sealed and the seal 368 can therefore be a non-hermetic seal or can be omitted altogether.

Figure 4:
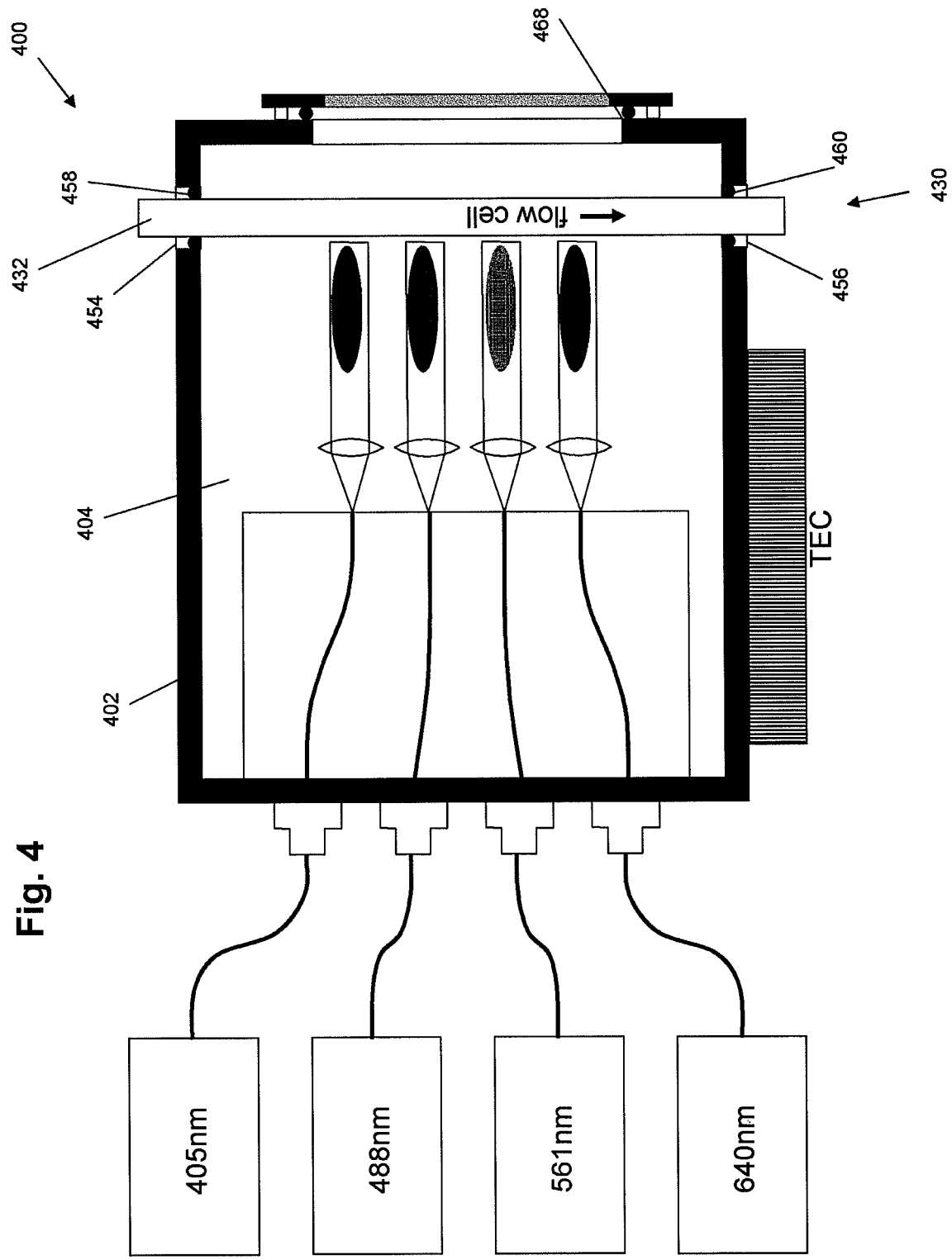
FIG. 4 schematically shows another optical system that can be used to direct light to samples for performing optical measurements such as laser-induced fluorescence and spectroscopic analysis.

FIG. 4 schematically shows an embodiment of an optical system 400 that can be used to direct light for optical measurements such as laser-induce fluorescence and spectroscopic analysis. The optical system 400 is similar to optical systems 100 and 300 in some aspects, and similar elements are labeled with the same reference numerals used in FIGS. 1 and 3 except that the numbers are increased by 200 and 100 respectively. Optical system 400 can include a flow cell connector 430 that attaches a flow cell 432 to the housing 402 so that the flow cell 432 passes through the housing 402. For example, the housing 402 can comprise two apertures 454, 456 and two flexible seals 458, 460, so that the flow cell 432 can be slidably inserted through the apertures 454, 456 and held in place by friction against the flexible seals 458, 460. Alternatively, the housing 402 can include a door allowing the housing 402 to be opened and the flow cell 432 to be placed inside. In some embodiments, the interior chamber 404 can be exposed to ambient air when flow cell 432 is removed and the seals 458, 460 can be non-hermetic seals. Also, the seal 468 can be a non-hermetic seal or can be omitted altogether.

A wide variety of other variations are possible. Components can be added, removed, and/or rearranged. For example, in some embodiments, the optical system does not include a thermally conductive housing or a thermoelectric controller. In some embodiments, the optical fibers can be oriented to direct light to the flow cell without the use of lenses or other optical elements. Other variations are also possible. Similarly, in any method or process disclosed herein, steps or operations can be add, removed, and/or rearranged.

Reference throughout this specification to "some embodiments," "certain embodiments," or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

Although the inventions presented herein have been disclosed in the context of certain preferred embodiments and examples, it will be understood by those skilled in the art that the inventions extend beyond the specifically disclosed embodiments to other alternative embodiments and/or uses of the inventions and obvious modifications and equivalents thereof. Thus, it is intended that the scope of the inventions herein disclosed should not be limited by the particular embodiments described above.

What is claimed is:

1. A laser system for directing light for optical measurements, the laser system comprising:
   a flow cell connector configured to receive a flow cell configured to provide a sample fluid for measurement;
   a housing defining an interior chamber, wherein the housing is thermally conductive;
   a plurality of optical fibers within the interior chamber, the plurality of optical fibers configured to receive light from a plurality of lasers disposed outside the housing, said optical fibers having a plurality of output ends;
   an optical fiber mount configured to orient the plurality of optical fibers with said output ends positioned to emit light toward said flow cell;
   a plurality of optical input ports coupled to the housing, the optical input ports configured to interchangeably couple to the plurality of lasers such that the plurality of optical fibers are configured to receive the light from the plurality of lasers through the optical input ports and such that the plurality of lasers are interchangeable with other lasers;
   a thermoelectric controller thermally coupled to the housing, wherein the thermoelectric controller is configured to maintain the interior chamber at a substantially constant temperature to reduce temperature instability and resulting pointing errors.

2. The laser system of claim 1, wherein each output end comprises a center, and wherein the optical fiber mount is configured to position the plurality of optical fibers with the centers of the output ends spaced about 110 to 140 micrometers apart.

3. The laser system of claim 2, wherein the optical fiber mount is configured to position the plurality of optical fibers with the centers of the output ends spaced about 125 micrometers apart.

4. The laser system of claim 1, wherein said plurality of optical fibers comprise a plurality of input ends, the input ends being distributed across a first distance, the output ends being distributed across a second distance, wherein the first distance is greater than the second distance.

5. The laser system of claim 1, wherein the plurality of optical fibers are polarization-maintaining optical fibers.

6. The laser system of claim 1, further comprising a flow cell attached to said flow cell connector.

7. The laser system of claim 1, further comprising:
   one or more optical elements configured to receive the light output by the plurality of optical fibers, to modify the light, and output a plurality of beams of light, wherein the flow cell connector is configured to position the flow cell to intersect the beams of light.

8. The laser system of claim 7, wherein the plurality of beams of light produced by said one or more optical elements comprise a plurality of substantially elliptical beams of light.

9. The laser system of claim 8, wherein the one or more optical elements comprise a plurality of anamorphic microlenses.

10. The laser system of claim 7, further comprising one or more output windows configured to transmit the beams of light out of the internal chamber.

11. The laser system of claim 10, wherein said flow cell connector is configured to attach the flow cell to the outside of said housing.

12. The laser system of claim 1, wherein the housing is sealed to insulate the interior chamber from ambient air.

13. The laser system of claim 1, wherein the plurality of optical input ports are configured to removably engage a plurality of input optical fibers to interchangeably couple to the plurality of lasers to the plurality of optical input ports.

14. The laser system of claim 1, wherein the plurality of optical input ports comprise a plurality of FC connectors.

15. The laser system of claim 1, wherein the plurality of optical input ports comprise a plurality of angle-polished connections.

16. The laser system of claim 1, further comprising:
   a plurality of input optical fibers coupled to said optical input ports; and
   a plurality of laser light sources coupled to said input optical fibers.

17. The laser system of claim 7, wherein the flow cell connector comprises thermally conducting material, said flow cell connector being thermally coupled to the thermoelectric controller, the thermoelectric controller configured to maintain the flow cell at a substantially constant temperature.

18. The laser system of claim 7, wherein the one or more optical elements are disposed in the housing, the one or more optical elements configured to transmit the light out of the internal chamber, and the flow cell connector is configured to attach the flow cell to the outside of the housing.

19. The laser system of claim 1, wherein the flow cell connector is configured to attach the flow cell to the housing with the flow cell passing through said interior chamber.

20. The laser system of claim 19, wherein the flow cell connector comprises at least one seal configured to form a seal around the flow cell.

21. The laser system of claim 1, wherein the housing has a volume of less than about 10 cubic inches.

22. A laser system for directing light for optical measurements, the laser system comprising:
   a flow cell connector configured to receive a flow cell configured to provide a sample fluid for measurement;
   a housing defining an interior chamber;
   a plurality of optical fibers within the interior chamber, the plurality of optical fibers configured to receive light from a plurality of lasers disposed outside the housing, said optical fibers having a plurality of output ends;
   an optical fiber mount configured to orient the plurality of optical fibers with said output ends positioned to emit light toward said flow cell;
   a plurality of optical input ports coupled to the housing, the optical input ports configured to interchangeably couple to the plurality of lasers such that the plurality of optical fibers are configured to receive the light from the plurality of lasers through the optical input ports and such that the plurality of lasers are interchangeable with other lasers;
   one or more lenses within the interior chamber, the one or more lenses configured to receive the light output by the plurality of optical fibers, to modify the light, and to output a plurality of beams of light;
   wherein the one or more lenses are configured such that the plurality of beams of light produced by the one or more lenses comprise a plurality of substantially elliptical beams of light;
   wherein each of the plurality of substantially elliptical beams of light have a long axis and a short axis, and wherein the flow cell connector is configured to position the flow cell such that each of the plurality of substantially elliptical beams of light intersect the flow cell with the long axis extending substantially laterally across the flow cell and with the short axis extending substantially longitudinally along the flow cell.

23. The laser system of claim 22, wherein the one or more lenses comprise a plurality of lenses positioned to receive the light output by the respective plurality of optical fibers.

24. The laser system of claim 22, wherein the one or more lenses comprise one or more anamorphic lenses.

25. A laser system for directing light for optical measurements, the laser system comprising:
   a flow cell connector configured to receive a flow cell configured to provide a sample fluid for measurement;
   a housing defining an interior chamber, wherein the housing is sealed to insulate the interior chamber from ambient air;
   a plurality of optical fibers within the interior chamber, the plurality of optical fibers configured to receive light from a plurality of lasers disposed outside the housing, said optical fibers having a plurality of output ends;
   an optical fiber mount configured to orient the plurality of optical fibers with said output ends positioned to emit light toward said flow cell; and
   a plurality of optical input ports coupled to the housing, the optical input ports configured to interchangeably couple to the plurality of lasers such that the plurality of optical fibers are configured to receive the light from the plurality of lasers through the optical input ports and such that the plurality of lasers are interchangeable with other lasers.

26. The laser system of claim 25, further comprising one or more optical elements within the interior chamber, the one or more optical elements configured to receive the light output by the plurality of optical fibers, to modify the light, and to output a plurality of substantially elliptical beams of light.

27. The laser system of claim 25, wherein the flow cell connector is configured to attach the flow cell outside the interior chamber of the housing.

28. A laser system for directing light for optical measurements, the laser system comprising:
   a flow cell connector configured to receive a flow cell configured to provide a sample fluid for measurement;
   a housing defining an interior chamber, wherein the flow cell connector is configured to attach the flow cell outside the interior chamber of the housing such that the flow cell is not disposed inside the interior chamber of the housing;
   a plurality of optical fibers within the interior chamber, the plurality of optical fibers configured to receive light from a plurality of lasers disposed outside the housing, said optical fibers having a plurality of output ends;
   an optical fiber mount configured to orient the plurality of optical fibers with said output ends positioned to emit light toward said flow cell; and
   a plurality of optical input ports coupled to the housing, the optical input ports configured to interchangeably couple to the plurality of lasers such that the plurality of optical fibers are configured to receive the light from the plurality of lasers through the optical input ports and such that the plurality of lasers are interchangeable with other lasers.

29. The laser system of claim 28, further comprising a thermoelectric controller thermally coupled to the housing, wherein the housing is thermally conductive, and wherein the thermoelectric controller is configured to maintain the interior chamber at a substantially constant temperature.

30. The laser system of claim 28, further comprising one or more optical elements within the interior chamber, the one or more optical elements configured to receive the light output by the plurality of optical fibers, to modify the light, and to output a plurality of substantially elliptical beams of light.

31. The laser system of claim 28, wherein the flow cell connector is configured to removably attach the flow cell to the housing such that the flow cell is interchangeable.

32. The laser system of claim 28, wherein the housing is sealed to insulate the interior chamber from ambient air.

* * * * *